(12) United States Patent
Tatarczyk et al.

(10) Patent No.: US 7,787,125 B2
(45) Date of Patent: Aug. 31, 2010

(54) APPARATUS FOR MEASURING A SPECTRAL DISTRIBUTION OF A PRINTED PRODUCT PRODUCED WITH A PRINTING DEVICE

(75) Inventors: Christina Tatarczyk, Groebenzell (DE); Joachim Tatarczyk, Groebenzell (DE)

(73) Assignee: Theta Systems Elektronik GmbH (DE)

( * ) Notice: Subject to any disclaimer, the term of this patent is extended or adjusted under 35 U.S.C. 154(b) by 43 days.

(21) Appl. No.: 11/732,093

(22) Filed: Apr. 2, 2007

(65) Prior Publication Data
US 2007/0229822 A1 Oct. 4, 2007

(30) Foreign Application Priority Data
Apr. 3, 2006 (DE) .................. 10 2006 015 375

(51) Int. Cl.
*G01N 21/55* (2006.01)
(52) U.S. Cl. .................. 356/445; 356/237.4; 356/328
(58) Field of Classification Search ... 356/237.2–237.6, 356/238.3, 239.3, 239.7, 328, 445
See application file for complete search history.

(56) References Cited
U.S. PATENT DOCUMENTS
5,037,201 A    8/1991  Smith, III et al.
5,486,919 A *  1/1996  Tsuji et al. ............... 356/237.4
5,724,259 A    3/1998  Seymour et al.
5,724,437 A    3/1998  Buecher et al.
6,040,909 A *  3/2000  Hasegawa et al. .......... 356/614
6,549,271 B2 * 4/2003  Yasuda et al. ................ 355/55

FOREIGN PATENT DOCUMENTS
DE   43 21 177 A1   1/1995
EP   1470918 A3     9/2005

* cited by examiner

Primary Examiner—Gregory J Toatley, Jr.
Assistant Examiner—Iyabo S Alli
(74) Attorney, Agent, or Firm—Gerald E. Hespos; Michael J. Porco

(57) ABSTRACT

An apparatus (10) measures a spectral distribution of a printed product (12) produced with a printing device. The apparatus (10) has an illuminating source (20) for illuminating the printed product (12), an optoelectronic measuring means (32) for measurer the reflectance value of a section of the spectrum of the light (26) reflected from the printed product (12), an optical disperser (28) for dispersing the wavelengths of the reflected light (26), and a light entry gap plane that is definitive for the disperser (28). The light entry gap plane that is definitive for the disperser (28) is created by the surface of the printed product (12) to be examined.

16 Claims, 2 Drawing Sheets

APPARATUS FOR MEASURING A SPECTRAL DISTRIBUTION OF A PRINTED PRODUCT PRODUCED WITH A PRINTING DEVICE

BACKGROUND OF THE INVENTION

1. Field of the Invention

The invention relates to an apparatus for measuring a spectral distribution of a printed product produced with a printing device, which comprises a illuminating means for illuminating the printed product, an optoelectronic measuring means for measuring the reflectance value of at least one section of the spectrum of the light reflected from the printed product, an optical dispersing means for dispersing the wavelengths of the reflected light, and a light entry gap plane that is definitive for the dispersing means.

2. Description of the Related Art

Various types of quality monitoring and control of printing processes are known in the graphics industry. One of the measuring methods used in this case is color measurement by means of an analysis of the spectral distribution of the light reflected from a printed product. Apparatus which measure spectrally resolve the spectrum of the reflected light in bandwidths of, for example, 20 or fewer nanometers and use these to determine the associated reflectance values. From the reflectance values, various characteristic color values can subsequently be derived. Breaking down the spectrum of the reflected light can be carried out by means of characteristic filters, prisms or diffraction gratings, gratings being preferred in modern apparatus because of their high resolution.

Various techniques are known to measure the reflected light broken down or diffracted by a diffraction grating in its various different spectral regions. In these techniques, amongst other things, the grating used is pivoted and in the process the light is directed onto a single photoelement. Alternatively, it is known to deflect a linear light beam, which is diffracted into a rectangular area, onto a diffraction grating through an entry gap. The light beam diffracted in this way is measured in this area by means of a line or surface sensor having a large number of photoelements. However, in all these apparatuses, complicated optics is needed between the product to be measured and the entry gap. Furthermore, optics, in particular prisms, is also needed between the grating and the measuring means.

The invention is based on the object of configuring an apparatus for measuring a spectral distribution of a printed product produced with a printing device of the type mentioned at the beginning more economically and more compactly with the same or improved measurement quality.

SUMMARY OF THE INVENTION

According to the invention, a generic apparatus for measuring a spectral distribution of a printed product produced with a printing device is improved with the effect that the light entry gap plane that is definitive for the dispersing means is created by the surface of the printed product to be examined itself. In other words, according to the invention the light beam tested by the measuring means is not that which is led to the measuring means through an entry gap but is a light beam which is reflected directly in linear form from the surface of the printed product to be tested.

With the solution according to the invention, an apparatus which can be produced, mounted and even maintained particularly economically is provided. This is done in that the measuring means of an apparatus for measuring a spectral distribution has led to it a gap-like or linear light beam about 1 mm to about 2 mm wide, which is reflected directly in this "gap form" from the surface of the printed product to be examined. The solution according to the invention can consequently dispense with complicated optics between the product and an entry gap of a spectroscope.

The invention is based, inter alia, on the finding that it is not necessary to illuminate the object to be examined over as large an area as possible and as homogeneously as possible but that point-like or locally limited illumination is considerably more practical if the region of the printed product which is illuminated to a limited extent is simultaneously used as an entry light beam for an apparatus according to the invention. In the apparatus, the entry light beam is subsequently diffracted, dispersed and broken down.

According to the invention, it is also possible to dispense with the entry gap or an entry gap aperture stop itself, specifically because the gap shape of the entry light beam that is definitive for the dispersing means is created by means of linear illumination of the printed product to be examined. The linear illumination can be created particularly advantageously by means of a cylindrical lens or optics and, if appropriate, an aperture stop in front of the illuminating means. In this case, considerably lower requirements have to be placed on the quality and the accuracy of these optical elements comprising cylindrical optics and aperture stop than in the case of known optics, as are provided between a product to be measured and an entry gap of known spectroscopes.

The illuminating means used for the apparatus according to the invention is particularly advantageously at least one light-emitting diode which, with low costs and little requirement for space, provides a large quantity of light. The plane of the illuminating light beam directed from the illuminating means onto the product to be measured is advantageously inclined at an angle of about 45° to the surface of the printed product and, in particular, also at an angle of about 45° to the viewing or observation direction of the measuring means. In this case, the viewing direction is simultaneously the direction of the gap-like light beam reflected from the printing product to the dispersing means, which is then diffracted at this dispersing means.

Preferred as dispersing means according to the invention is a diffraction grating which, as mentioned at the beginning, permits a high resolution of the spectral distribution. The preferred grating is a transmission grating. Alternatively, a reflection grating can also be used. If necessary, prisms or characteristic filters can also be used but distinct preference given to the transmission grating because of the compact design of the apparatus according to the invention which can be achieved therewith.

The preference for a transmission grating is also based not least on the fact that, in the apparatus according to the invention, only one projection lens or optics is also preferably arranged between the measuring means and the dispersing means. According to the invention, on the other hand, complicated prism systems, as are provided in this region in the case of known spectroscopes, are deliberately omitted.

This omission is possible since, according to the invention, the measuring means used is in particular a sensor which has a large number of photoelements and can accordingly offer high resolution. The measuring means used is particularly preferably an inexpensive surface sensor, as is known from conventional digital cameras for image recordings.

The apparatus according to the invention can, moreover, be configured particularly compactly and without complex prism optics in the beam path by the arrangement formed from optoelectronic measuring means and optical dispersing means, and in particular also from the projection optics, being oriented in its longitudinal direction obliquely with respect to the direction of the light beam reflected from the printed product and incident on the dispersing means. The arrangement is in particular advantageously set obliquely at an angle of between about 20° and about 40° to the direction of the light beam incident on the dispersing means.

To improve the apparatus according to the invention further with regard to its measuring accuracy, an aperture stop preferably is provided above the surface of the printed product for holding back external light reflected from the printed product.

Finally, to increase the measuring accuracy in the case of a flat printed product, which can in particular be web-like, in that region which is examined by the measuring means, support for the printed product is ensured. The support ensures that the position of the printed product or its distance relative to the rest of the apparatus does not change. In particular, the printed product is held in such a way that, although it can move past under the illuminating means and the dispersing means as a web, the position of the illuminated light strip does not change in the process. Such support preferably is created by means of a supporting roller, whose axis of rotation is arranged in the direction of the reflected light beam under the printed product at the point of the region of the latter illuminated in a strip-like manner.

In the following text, an exemplary embodiment of an apparatus according to the invention will be explained in more detail by using the appended schematic drawings.

DETAILED DESCRIPTION OF THE PREFERRED EMBODIMENT

Figure 1:
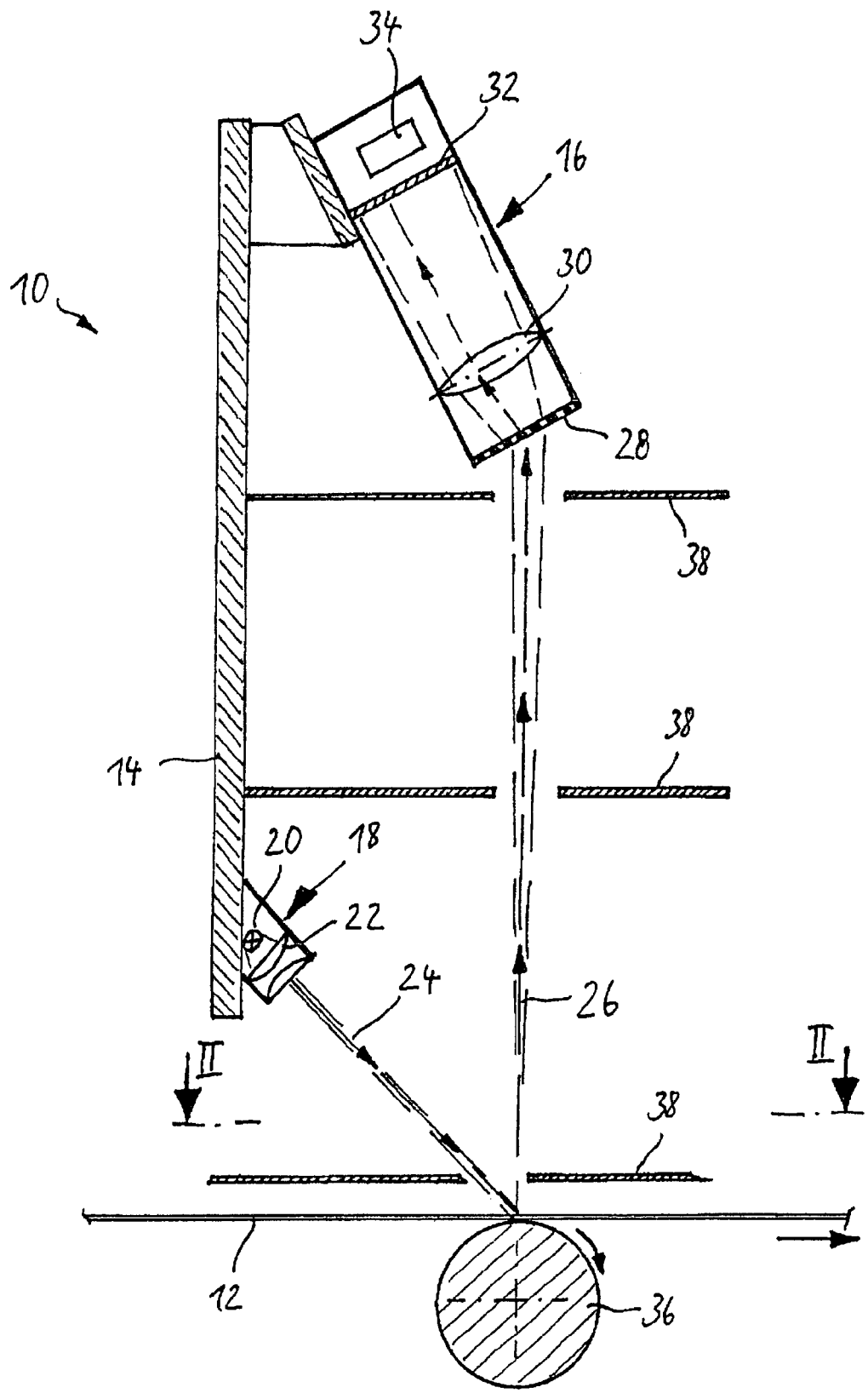
FIG. 1 shows a longitudinal section of an exemplary embodiment of an apparatus according to the invention for measuring a spectral distribution of a printed product produced with a printing device.
Figure 2:
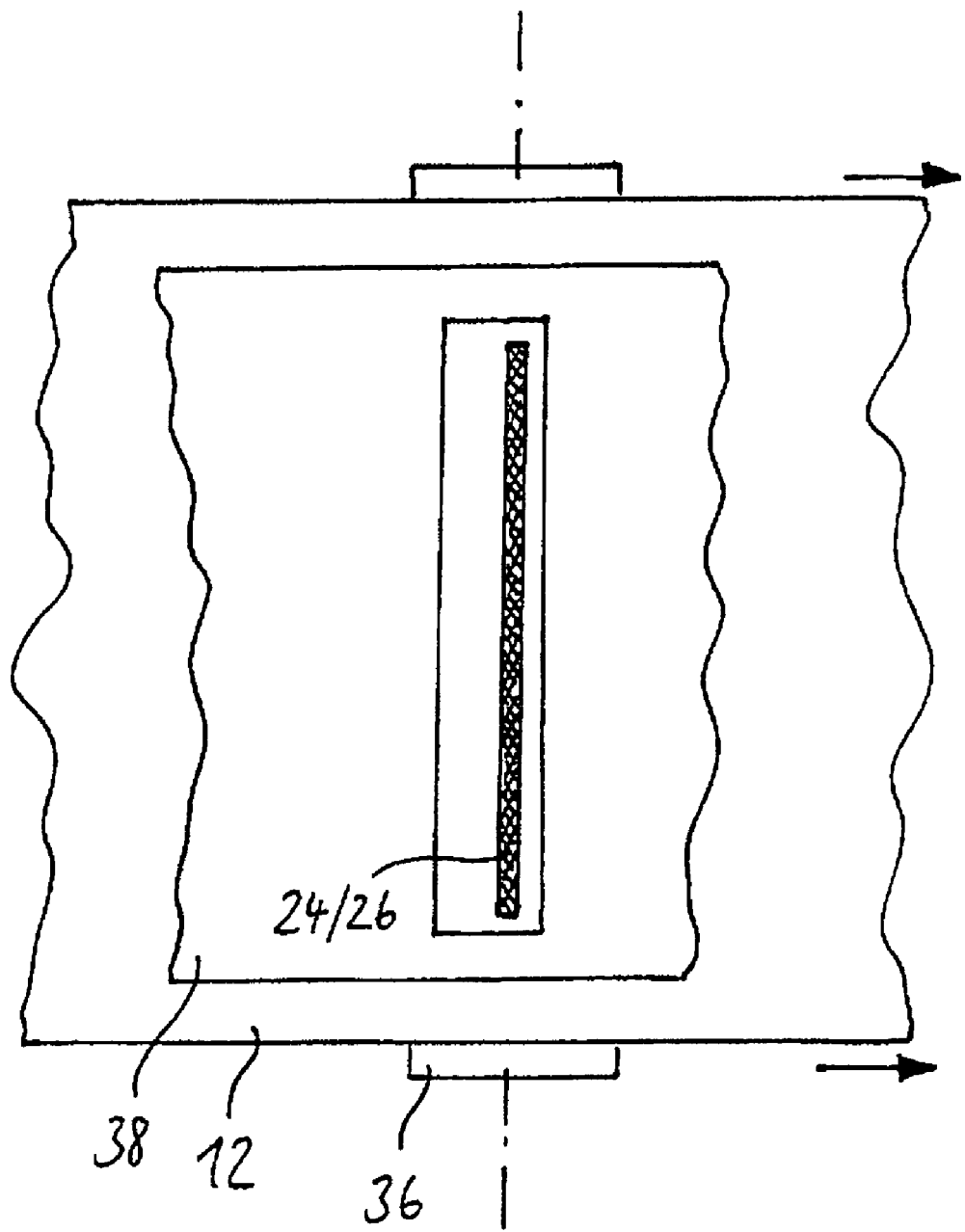
FIG. 2 is a section taken along line II-II in FIG. 1.

In the figures, an apparatus 10 for monitoring the quality of a flat printed product 12 produced with a printing device, not shown further, is illustrated. The printed product 12 is web-like and, in relation to the figures, is moved through under the apparatus 10 from left to right. On the printed product 12 there are printed graphic figures, which are to be tested with regard to the quality of their printed image.

The apparatus comprises a rod-like holder 14 which is oriented substantially vertically and in whose upper end section a camera unit 16 is mounted and in whose lower end section an illuminating unit 18 is mounted.

The illuminating unit 18 comprises an illuminating means 20 in the form of a light-emitting diode emitting white light, in front of which cylindrical optics 22 is arranged in the beam path. The cylindrical optics 22 focuses the light emitted by the light-emitting diode 20 to form a strip-like or gap-like illuminating light beam 24 which is about 1 mm to 2 mm wide and whose beam plane is directed at an angle of about 45° directly onto the surface of the printed product 12 to be examined.

From the surface of the printed product 12 illuminated in a strip-like manner in this way, a likewise strip-like or gap-like light beam 26 is reflected in the direction of the camera unit 16. The main radiation direction of the light beam 26 is in this case directed approximately at an angle of 90° to the surface or plane of the flat printed product 12.

The light beam 26 strikes the camera unit 16 at a dispersing means 28 in the form of a diffraction grating. At this dispersing means 28, the spectrum of the light beam 26 reflected from the printed product 12 is broken down and diffracted and, as a "fanned out" light beam 26, passes on further to a projection optics 30 arranged in the interior of the camera unit 16. Using this projection optics 30, the alignment of the reflected and diffracted light beam 26 is corrected slightly in order that it covers as extensively as possible a measuring means 32 in the form of a rectangular surface sensor located behind the projection optics 30. In this case, the measuring means 32 is provided with a large number of individual photoelements, which are able to report the luminous intensity of the incident light individually to evaluation electronics 34 arranged behind the measuring means 32.

In this case, together with its dispersing means 28, its projection optics 30 and its measuring means 32, the camera unit 16 is placed obliquely at an angle of about 30° to the longitudinal direction of the reflected light beam 26 in such a way that the light diffracted by the dispersing means 28 is projected onto the measuring means 32 over virtually the entire area without complicated optical correcting means, such as prisms.

To improve the measuring accuracy of the entire apparatus 10, the flat printed product 12 is supported underneath in the region illuminated by the illuminating light beam 24 by means of a supporting device 36 in the form of a supporting roller. Furthermore, around the illuminating light beam 24 and the reflected light beam 26, at a suitable distance, a total of three aperture stops 38 are also arranged in a substantially parallel orientation with respect to the surface of the printed product 12, with which stops external light is kept away from the dispersing means 28 of the camera unit 16.

In conclusion, it should be noted that all the features which are cited in the application documents and in particular in the dependent claims, despite the formal references made to one or more specific claims, are also intended to be assigned individual protection individually or in any desired combination.

What is claimed is:

1. Apparatus (10) for measuring a spectral distribution of a printed product (12) produced with a printing device, comprising:

a support (14);

an illuminating means (20) fixedly mounted to the support (14) for emitting light, optic means (22) fixed relative to the illuminating means (20) for focusing the light emitted from the illuminating means (20) into a light beam (24), directing the light beam (24) onto the printed product (12) at an acute angle to a surface of the printed product and producing a reflected light beam (26) reflected substantially perpendicularly from the surface of the printed product (12), and an arrangement (16) fixedly mounted on the support (14) and supported in fixed relationship relative to the illuminating means (20) and the optic means so that the arrangement disposed for receiving the reflected light beam (26), the arrangement (16) including an optical dispersing means (28) with a surface aligned at an acute angle to the reflected light beam (26) and disposed for receiving the reflected light beam (26) and dispersing wavelengths of reflected light beam (26), an optoelectronic measuring means (32) fixed in the arrangement (16) for measuring a reflectance value of a section of the spectrum of the reflected light beam (26) dispersed by the optical dispersing means (28), the reflected light beam (26) defining a light entry gap plane that extends directly from the surface of the printed product (12) to be examined to the dispersing means (28).

2. Apparatus according to claim 1, characterized in that the gap shape of the reflected light (26) that is definitive for the dispersing means (28) is created by means of linear illumination (20, 22, 24) of the printed product (12) to be examined.

3. Apparatus according to claim 2, characterized in that the illumination (20, 22, 24) of the printed product (12) is configured by means of at least one light-emitting diode.

4. Apparatus according to claim 3, characterized in that the dispersing means (28) is configured with a diffraction grating.

5. Apparatus according to claim 4, characterized in that only one projection optics (30) is arranged between the measuring means (32) and the dispersing means (28).

6. Apparatus according to claim 5, characterized in that the measuring means (32) is configured as a surface sensor.

7. Apparatus according to claim 6, characterized in that the arrangement (16) formed from the measuring means (32) and the dispersing means (28), and in particular also from the projection optics (30), is oriented in its longitudinal direction obliquely with respect to the direction of the light beam (26) reflected from the printed product (12) and incident on the dispersing means (28).

8. Apparatus according to claim 7, characterized in that an aperture stop (38) for holding back external light reflected from the printed product (12) is provided above the surface of the printed product (12).

9. Apparatus according to claim 8, characterized in that the printed product (12) is flat, and is examined by the measuring means (32) in a region in which it is supported by means of a supporting device (36).

10. Apparatus according to claim 1, characterized in that the illumination (20, 22, 24) of the printed product (12) is configured by means of at least one light-emitting diode.

11. Apparatus according to claim 1, characterized in that the dispersing means (28) is configured with a diffraction grating.

12. Apparatus according to claim 1, characterized in that only one projection optics (30) is arranged between the measuring means (32) and the dispersing means (28).

13. Apparatus according to claim 1, characterized in that the measuring means (32) is configured as a surface sensor.

14. Apparatus according to claim 1, characterized in that the arrangement (16) formed from the measuring means (32) and the dispersing means (28), and in particular also from the projection optics (30), is oriented in its longitudinal direction obliquely with respect to the direction of the light beam (26) reflected from the printed product (12) and incident on the dispersing means (28).

15. Apparatus according to claim 1, characterized in that an aperture stop (38) for holding back external light reflected from the printed product (12) is provided above the surface of the printed product (12).

16. Apparatus according to claim 1, characterized in that the printed product (12) is flat, and is examined by the measuring means (32) in a region in which it is supported by means of a supporting device (36).

* * * * *

UNITED STATES PATENT AND TRADEMARK OFFICE
CERTIFICATE OF CORRECTION

| | | |
|---|---|---|
| PATENT NO. | : 7,787,125 B2 | Page 1 of 1 |
| APPLICATION NO. | : 11/732093 | |
| DATED | : August 31, 2010 | |
| INVENTOR(S) | : Christina Tatarczyk | |

It is certified that error appears in the above-identified patent and that said Letters Patent is hereby corrected as shown below:

Title Page, Item (73) should read -

(73) Assignee: Theta System Elektronik GmbH (DE)

Signed and Sealed this
Twenty-sixth Day of April, 2011

David J. Kappos
*Director of the United States Patent and Trademark Office*